(12) United States Patent
Deroberts

(10) Patent No.: US 9,126,034 B1
(45) Date of Patent: *Sep. 8, 2015

(54) FLEXIBLE, WEARABLE THERAPEUTIC LASER ARRAY

(71) Applicant: Richard Ogden Deroberts, Wardensville, WV (US)

(72) Inventor: Richard Ogden Deroberts, Wardensville, WV (US)

(*) Notice: Subject to any disclaimer, the term of this patent is extended or adjusted under 35 U.S.C. 154(b) by 0 days.

This patent is subject to a terminal disclaimer.

(21) Appl. No.: 14/271,511

(22) Filed: May 7, 2014

Related U.S. Application Data

(63) Continuation-in-part of application No. 13/690,706, filed on Nov. 30, 2012, now Pat. No. 8,784,462.

(51) Int. Cl.
*A61N 5/06* (2006.01)
*A61N 5/067* (2006.01)
*A61N 5/00* (2006.01)

(52) U.S. Cl.
CPC .............. *A61N 5/06* (2013.01); *A61N 2005/005* (2013.01); *A61N 2005/067* (2013.01); *A61N 2005/0628* (2013.01); *A61N 2005/0652* (2013.01)

(58) Field of Classification Search
CPC ................... A61N 5/0616; A61N 2005/0652; A61N 2005/0659; A61N 2005/0662
USPC ....................................................... 607/88–94
See application file for complete search history.

(56) References Cited

U.S. PATENT DOCUMENTS

| | | | |
|---|---|---|---|
| 2010/0106077 A1* | 4/2010 | Rabin et al. ...................... | 604/20 |
| 2012/0226268 A1* | 9/2012 | Liu et al. ............................ | 606/9 |
| 2014/0276248 A1* | 9/2014 | Hall et al. .......................... | 601/2 |

* cited by examiner

*Primary Examiner* — Aaron Roane

(57) ABSTRACT

Method of producing a therapeutic laser or LED device (TLD). The TLD includes flexible membranes which comprise a high pressure air cavity. High air pressure is produced by fans which are computer speed controlled. Standoff posts provide a separation function between the TLD and the patient. Semiconductor laser diodes and lens sets or LEDs and lens sets in a two dimensional array produce the therapeutic light. Cooling air tubes direct air controlled by temperature sensors from the high pressure cavity onto laser diodes or LEDs. Capacitive proximity sensors in conjunction with infrared radiation sensors confirm close contact with a patient and allow light radiation. Power is supplied either by battery or by connection to mains power. A wireless touch screen device displays information to the user and controls the therapy session. The TLD and the power supply both have stretchable straps enabling the TLD to be fixed to the patient.

5 Claims, 16 Drawing Sheets

Generalized action spectrum for LLLT effects in cells, animals and patients.

FLEXIBLE, WEARABLE THERAPEUTIC LASER ARRAY

CROSS-REFERENCE TO RELATED APPLICATIONS

Ser. Nos. 13/690,706 14/036,739 PCT/US13/71371

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Technical Field of Invention

Embodiments in accordance with the invention relate generally to phototherapy. Phototherapy is a therapeutic physical modality using photons from the visible and infrared spectrum for tissue wound and burn healing, pain reduction, rhytide reduction (skin wrinkle) and hair follicle growth. It has also been shown to induce adipose cell membrane pore creation thereby allowing triglycerides, glycerol and free fatty acids to transit across the membrane into interstitial space. There have been more than 4000 studies published worldwide on the benefits of low level laser therapy (LLLT) and the effects observed with therapeutic lasers. Photo-biomodulation increases ATP synthesis by changing the oxidation/reduction status of the mitochondria and activates the sodium/potassium pump thereby altering cell membrane permeability to calcium. Cell growth has been stimulated by an increase in cell metabolism. Higher levels of cell regeneration have been documented. LLLT has been shown to stimulate nerve function and the production of nitric oxide and endorphins. The neuropeptide substance P (SP) and histamine have been shown to be reduced thereby reducing local inflammatory response. LLLT also reduces the formation of acetylcholine, and bradikynin. LLLT has also been shown to reduce fibrous tissue formation. In photodynamic therapy (PDT) a photosensitizer is mixed with antibodies that are targeted to antigens on abnormal tissue. This mixture is then administered to the patient and binds with the antigens. Radio magnetic radiation having a wavelength corresponding to the absorption wavelength of the photosensitizer is then administered to the patient. This treatment reduces the size of the abnormal tissue.

2. Description of Related Art

Low level laser therapeutic instruments (LLLTI) achieve their therapeutic effect by emitting laser or light emitting diode (LED) radiation at a chosen frequency or frequencies at a chosen power level for a chosen period of time at a chosen distance over a chosen area. Generally laser or LED power is measured in watts, area is measured in centimeters (cm) squared, distance is measured in centimeters and time is measured in seconds. Therapeutic dosage is measured in watts multiplied by seconds divided by area in cm squared. Watts multiplied by seconds is defined as joules so dosage then is joules/$cm^2$. From this we see that to apply a larger dosage to the same area we can either increase the power of the laser or LED or the length of time the laser or LED light is applied, or both. Small hand held LLLTI require more time for the treatment of a given area because they must be moved repeatedly. However, small hand held laser instruments are useful for treating areas which are curved or have small hollows. Larger LLLTI with many more lasers or LEDs cover a greater area but require cumbersome cooling apparatus to keep the lasers or LEDs from overheating. Because most large LLLTI are not flexible they do not apply an even and precise dosage to any part of the treatment area which is curved or contains small hollows. In the case of both small LLLTI and most large area LLLTI patients are required to remain still, (seated or lying), while the treatment is applied. This is so because the instruments are held in place by either the patient's or technician's hand or laid onto the patient in a horizontal manner and kept in place by gravity. In the case of scanning LLLTI the laser beam is spread over a large area and requires a high power laser applied for a long period of time to administer the same dosage. Scanning LLLTI do not apply an even and precise dosage pattern because the laser diode is not a constant distance from the entire treatment area and because a scan line contains more laser energy in the center of the scan line than at either of the ends of the scan line. None of the LLLTI designs discussed above are easily transported and none of them can be used by a patient while performing typical household or office functions. Generally LLLTI require connection to mains power at the wall and have control systems which are floor standing. This limits the ability of a patient to move about or in most cases even sit up.

Several newer LLLTI designs have the ability to conform to the contours of a patient's body but are problematic for several reasons. These LLLTI position the lasers or LEDs in contact with the patient's skin or very close to the skin. This positioning concentrates the laser or LED beam in a small diameter at the center of the treatment area because the beam does not have room to expand over the entire treatment area. Some designs employ vertical cavity surface emitting lasers (VCSEL) or horizontal cavity surface emitting lasers (HCSEL) devices. These lasers project a very narrow beam with almost no beam divergence and cannot spread their light energy over the entire treatment area without optical lenses which these LLLTI do not employ. In addition these designs are made of non-breathable materials held in direct contact with the skin. In some cases these LLLTI are intended to be worn for many hours at a time and in some cases days at a time. This can cause skin rashes, be extremely uncomfortable, retard blood flow in the area, and cause sweating which can attenuate the laser or LED light. Some of these LLLTI are programmed to energize at specific time intervals during the day and night. If the LLLTI has been removed by the patient in order to bathe or because of discomfort the LLLTI will not recognize this and run its programmed course of treatment without the patient being involved.

All LLLTI designs using lasers discussed above are problematic for eye safety. Laser light can damage the eye very quickly even at low power levels. Laser light in the visible spectrum is obvious to operator and patient and can be avoided with care. Laser light or LED light in the infrared spectrum is problematic because it is not obvious and does not cause pain until great damage has been done.

All semiconductor lasers and LEDs produce heat when energized. Edge emitting lasers produce more heat than VCSEL or HCSEL devices or LEDs because they are less efficient. Heat causes lasers to reduce their laser power output and to shift their laser light frequency to longer wavelengths. Referring to FIG. 17 of the drawings it is shown that physiological activity affected by laser light or LED light energy is not uniform but is greater in certain wavelengths than others. Also it is shown that by changing the frequency only slightly the effect of the laser light can be reduced by 80% or more. This reduction of the light affect combined with the reduction of power output of the laser caused by rising temperature can render the LLLTI completely ineffective. Automatic power control systems which monitor the laser power output and try to maintain a constant power output exacerbate the problem by increasing the electrical energy supplied to the laser diode thereby further increasing the heat generated. Without cooling, laser diodes can 'run away' and burn out immediately or have their life span reduced dramatically. The temperature of a patient's treatment area can vary significantly. The temperature of the hand or foot can be 20 degrees Fahrenheit cooler than the chest. Also room temperature will cause differences in skin temperature. Different body physiques will cause significant differences in skin temperature from one patient to the next. The only way to ensure that the laser diodes or LEDs are radiating at the optimum frequency is with active temperature control.

BRIEF SUMMARY OF THE INVENTION

A typical embodiment in accordance with the invention provides a method of producing a therapeutic laser or light emitting diode device (TLD). The TLD includes a stretchable, flexible membrane (1). This membrane is bonded to a second narrow, stretchable, flexible closed cell membrane (11) which in turn is bonded to a flexible, non-stretchable membrane (9). This structure comprises a high pressure air cavity. This structure has bonded to it high pressure fans. The high pressure fans are speed controllable. The fans are regulated by a sensor and voltage data computer processor connected to a power supply and computer control with wireless communication coupled to an electrical cable for power and data communication. The flexible, non-stretchable membrane (9) has attached to it a flexible membrane with bonded flat braided and/or non-braided electrical conductors (10). The flexible, non-stretchable membrane (9) is attached to the flexible membrane with bonded flat braided and/or non-braided electrical conductors (10) by means of standoff posts which penetrate and hold together the two membranes. The standoff posts provide, in addition to their attachment function, a separation function between the TLD and the surface area to be treated on a patient. The flexible membrane with bonded flat braided and/or non-braided electrical conductors (10) has coupled to it semiconductor laser diodes and lens sets (7) and automatic power control circuit electronic modules (21) or light emitting diodes and lens sets (29) in a two dimensional array. The flexible membrane with bonded flat braided and/or non-braided electrical conductors (10) is coupled to an electrical cable for power and data communication (14). The flexible, non-stretchable membrane (9) and the flexible membrane with bonded flat braided and/or non-braided electrical conductors (10) are pierced by cooling air tubes and spacers. The cooling air tubes and spacers direct air from the high pressure air cavity onto the emission side of the semiconductor laser diode and lens sets or LED and lens sets. The cooling air tubes and spacers also provide a spacer function between the stretchable, flexible closed cell membrane (1) and the flexible, non-stretchable membrane (9). The semiconductor laser diodes and lens sets are comprised of a semiconductor laser diode and a collimating lens and a planoconcave lens. The LED and lens sets are comprised of a light emitting diode and a collimating lens and a plano-concave lens. To ensure that radiant light energy is always disabled when the TLD is not in close contact with a patient's treatment area capacitive proximity sensors in conjunction with infrared radiation sensors transmit data to the sensor and voltage data computer processor which in turn sends instructions through the electrical cable for power and data communication to the power supply and computer control with wireless communication. The standoff posts and the cooling air tubes and spacers are held in place on the emission side of the semiconductor laser diode and lens sets or the LED and lens sets by flexible membrane washers. The temperature of the semiconductor laser diode and lens sets or the LED and lens sets is monitored by temperature sensors and this data is transmitted to sensor and voltage data computer processor which increases or decreases the speed of the one or more high pressure fans. The power supply and computer control with wireless communication can provide power either by battery or by connection to mains power at the wall. The power supply and computer control with wireless communication contains a key lock, a laser radiation full duration indicator light and a laser radiation momentary at start audible signal device. The one or more high pressure fans receive power from the power supply and computer control with wireless communication through the electrical cable for power and data communication. The sensor and voltage data computer processor analyzes all voltage levels using reference voltage technology and transmits instructions to the power supply and computer control with wireless communication through the electrical cable for power and data communication to adjust the voltages within specified ranges or sends a voltage-out-of-range signal to the power supply and computer control with wireless communication which then terminates the therapy session and initiates warning messages. A touch screen computerized device with wireless communication displays information to the user, communicates with the power supply and computer control with wireless communication, initiates a therapy session, terminates a therapy session, maintains therapy duration timing, displays to the user the elapsed time and the time left in the therapy session, displays to the user battery charge level and prohibits the initiation of a therapy session if battery charge is below a prescribed level, lets a user set therapy duration, lets a user set light power level, lets the user set the total therapy dosage, calculates the light power level and therapy duration based on total therapy dosage, lets the user choose between continuous or pulsed light operation, stores previous therapy session data and lets the user select a previously stored therapy regimen, lets a medical professional transmit a therapy regimen to the touch screen computerized device with wireless communication via the internet or cellular telephone and monitor the status of the TLD and the number of therapy sessions completed, sounds an audible signal when a therapy session is initiated, sounds an audible signal when a therapy session is terminated, waits a standard length of time after the audible signal before powering the lasers or LEDs, determines the correct positioning of the TLD with respect to the users treatment area using data input from the capacitive proximity sensor and the infrared radiation sensors, terminates a therapy session in the case the TLD becomes separated from the user's treatment area and sounds an audible alarm, warns the user of problems encountered by the TLD, shuts the TLD down in the event of malfunction, lets the user pause the therapy session and restart the therapy session, displays a standard laser warning message about laser safety, maintains a constant communication dialog with the power supply and computer control and in the event the communication dialog is broken the power supply and computer control terminates the therapy session. The communication transmission between the computerized device with wireless communication and the power supply and computer control with wireless communication is encrypted for security as is the transmission over the internet or cellular phone. The touch screen computerized device with wireless communication is either a made for purpose device programmed to perform the functions described above and provided with the TLD or it is an application program loadable to a cellphone, touch screen tablet, lap top computer or a desk top computer which has been approved and certified as being capable of performing the stated functions. The TLD and the power supply and computer control with wireless communication both have stretchable straps with hook and loop fasteners. The stretchable straps with hook and loop fasteners enable the TLD to be fixed to the patient in a manner that allows movement of the area to be treated and movement of the patient within and without the treatment premises. The stretchable straps are connected to the TLD with zippers to enable quick removal for cleaning and replacement. The movement of the patient must not exceed the maximum range of the communication capability between the power supply and computer control with wireless communication and the touch screen computerized device with wireless communication or the therapy session will be terminated by the power supply and computer control with wireless communication.

DETAILED DESCRIPTION OF THE INVENTION

Figure 1:
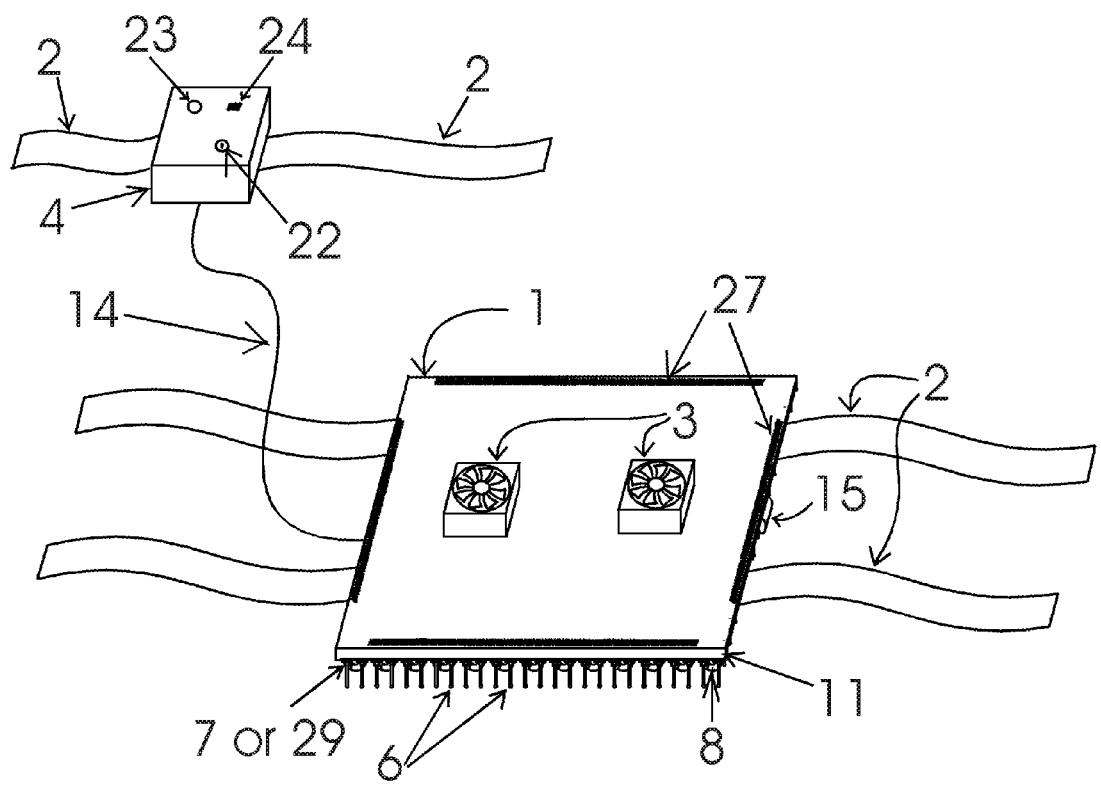
FIG. 1 is a view showing one possible embodiment of the present invention with all the major assemblies depicted in a usable arrangement.

The following references to the drawings are discussed in the narrative below.

1 Stretchable, flexible closed cell membrane
2 Stretchable straps with hook and loop fasteners
3 High pressure fan with speed control and air filter
4 Power supply and computer control with wireless communication
5 Touch screen computerized device with wireless communication
6 Standoff post
7 Semiconductor laser diode and lens set
8 Cooling air tube and spacer
9 Flexible, non-stretchable membrane
10 Flexible membrane with bonded flat braided and/or non-braided electrical conductors 11 Narrow, stretchable, flexible closed cell membrane
12 Flexible membrane washer
13 High pressure air cavity
14 Electrical cable for power and data communication
15 Capacitive proximity sensor
16 Infrared radiation sensor
17 Collimating lens
18 Plano-concave lens
19 Semiconductor laser diode
20 Temperature sensor
21 Automatic power control circuit electronic modules
22 Key lock
23 Laser radiation full duration indicator light
24 Laser radiation momentary at start audible signal device
25 Flat braided and/or non-braided electrical conductors
26 Holes in flexible, non-stretchable membrane
27 Zipper attachment for stretchable straps with hook and loop fasteners
28 Sensor and voltage data computer processor
29 Light emitting diode and lens sets
30 Light emitting diode The present disclosure relates to producing a therapeutic laser or light emitting diode device. Specific examples of membranes, layer configuration, materials, and other arrangements are described below to simplify the present disclosure. These are, of course, merely examples and are not intended to limit the invention from that described in the claims.

Referring now to FIG. 1 of the drawings, the reference numeral (1) refers to a stretchable, flexible closed cell membrane. The term stretchable in this context means the ability to elongate at least 10% of its length without permanently deforming. The term flexible in this context means the ability to bend in an arc with radius of 4 inches or less without permanently deforming. The term closed cell membrane in this context means a material similar to polyethylene foam, neoprene foam, polystyrene foam and others. The membrane (1) has mounted on it one or more high pressure fans with speed control and air filters reference numeral (3), which draw air in from above and force it beneath membrane (1).

Figure 2:
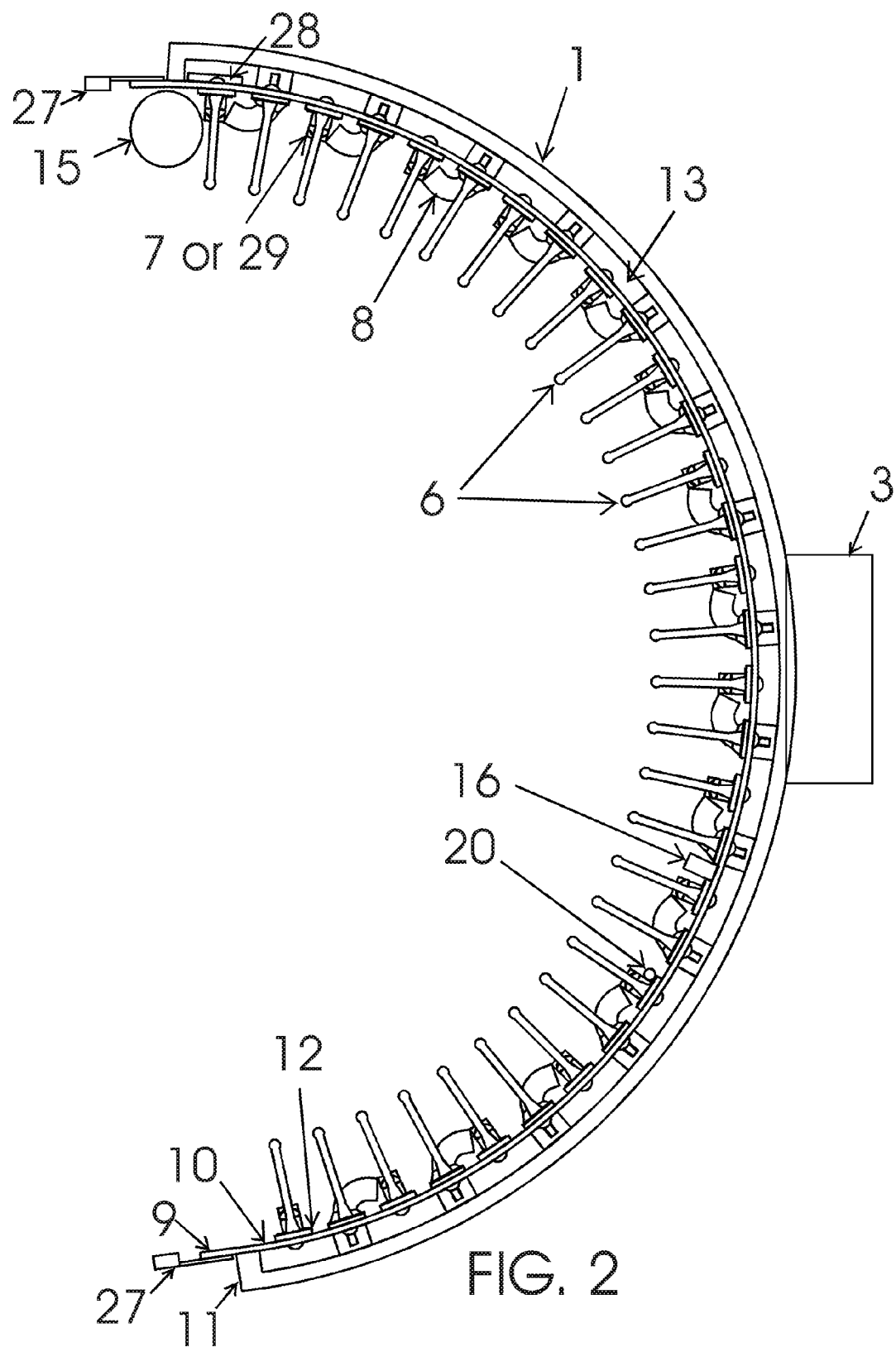
FIG. 2 is a side view of the present invention showing in more detail the sub-assemblies of the TLD in a flexed position.
Figure 3:
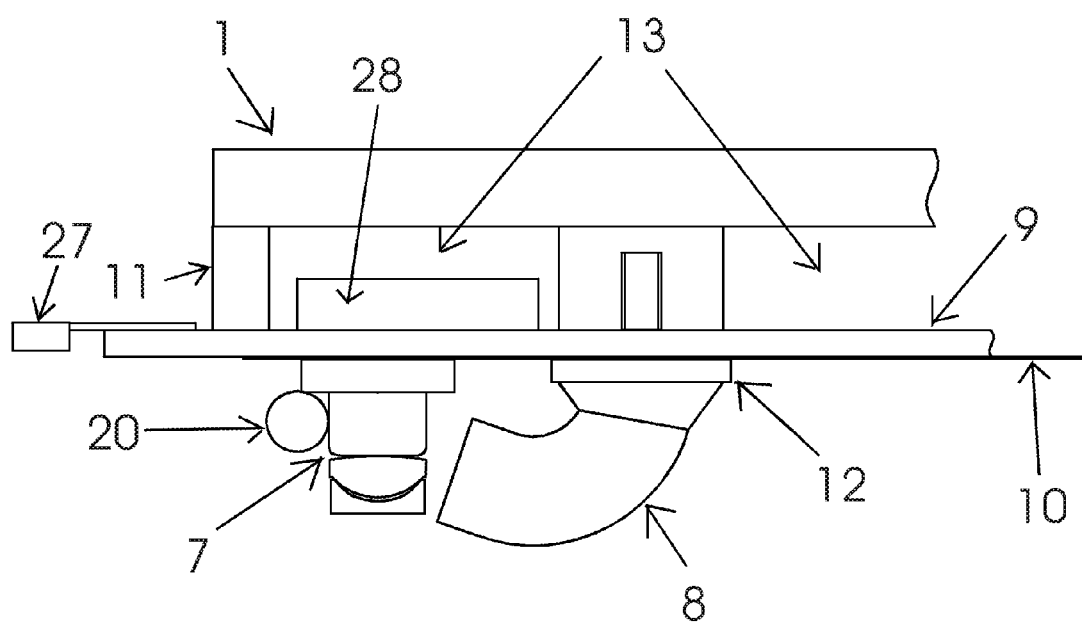
FIG. 3 is a side view of the present invention showing in detail the arrangement of the cooling air tube and spacer in relation to the semiconductor laser diode and lens sets, the high pressure air cavity, the temperature sensors and the sensor and voltage data computer processor.
Figure 5:
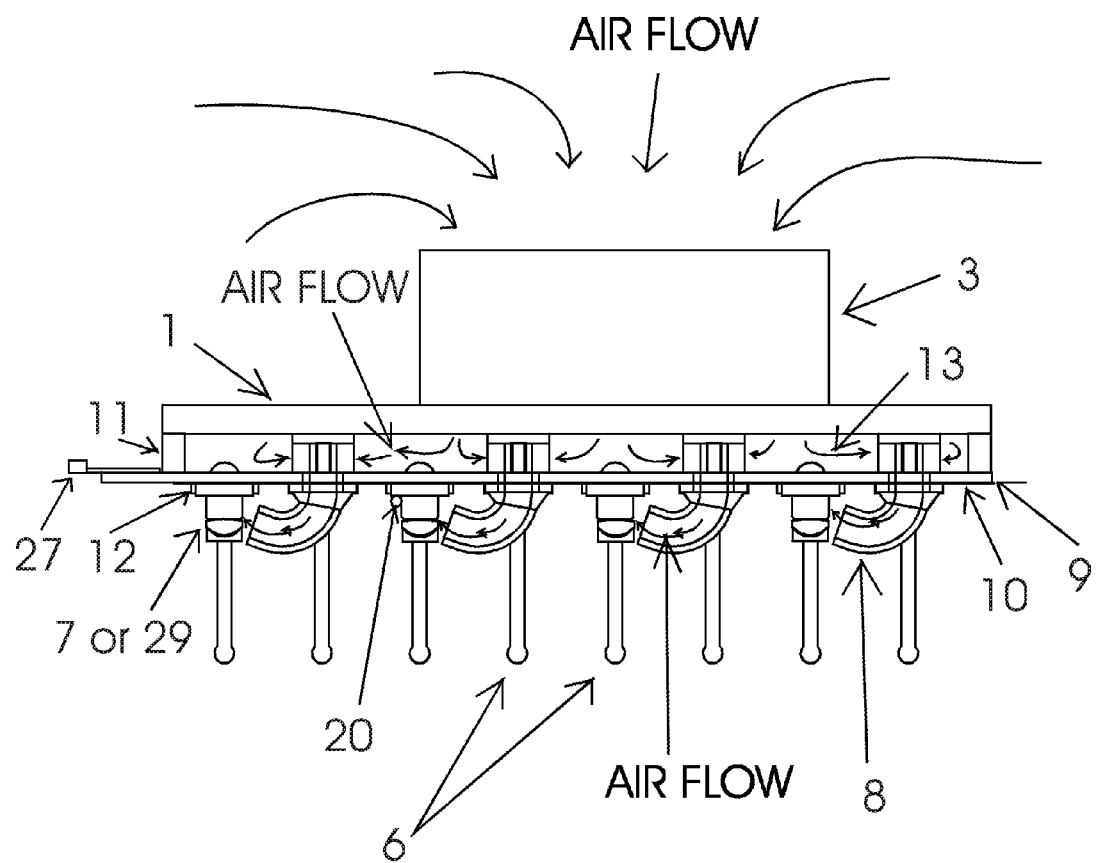
FIG. 5 is a side view of the present invention showing in detail the cooling air flow through the high pressure fan with speed control and air filters, the high pressure air cavity, the cooling air tubes and spacers and onto the semiconductor laser diodes and lens sets or the LEDs and lens sets.

Referring now to FIG. 2 and FIG. 3 and FIG. 5 of the drawings, the reference numeral (11) refers to a narrow stretchable, flexible closed cell membrane bonded to membrane (1). Reference numeral (9) refers to a flexible, non-stretchable membrane bonded to membrane (11). The term non-stretchable in this context means the inability to stretch more than 5% of the amount of elongation of the stretchable, flexible closed cell membrane when applying the same tensile force. Examples of this type of material are Viton, butyl, hypalon, EPDM, and others. The arrangement of membranes (1) and (11) and (9) form a high pressure air cavity shown as reference numeral (13). The air trapped in (13) is forced into the tops of the one or more cooling air tubes and spacers shown as reference numeral (8). The tops of the one or more air tubes (8) provide a supporting/spacing function to keep air cavity (13) open between membrane (1) and membrane (9). The air forced into the tops of one or more air tubes (8) is then forced down through the one or more air tubes (8) and onto the light emitting side of the one or more semiconductor laser diodes and lens sets shown as reference numeral (7) or LED and lens sets shown as reference numeral (29). This forced air in addition to cooling the one or more semiconductor laser diodes and lens sets or LED and lens sets provides a cooling and drying effect on the patient's treatment area thereby enhancing comfort and preventing moisture from attenuating the light beams. The term high pressure in this context means a varying air pressure greater than the surrounding atmospheric pressure and capable of forcing air through the one or more air tubes (8) in a manner sufficient to cool the one or more semiconductor laser diodes and lens sets or LED and lens sets. Reference numeral (28) refers to the sensor and voltage data computer processor which analyzes data from the temperature sensors, the infrared sensors, the capacitive proximity sensors and all voltages.

Figure 7:
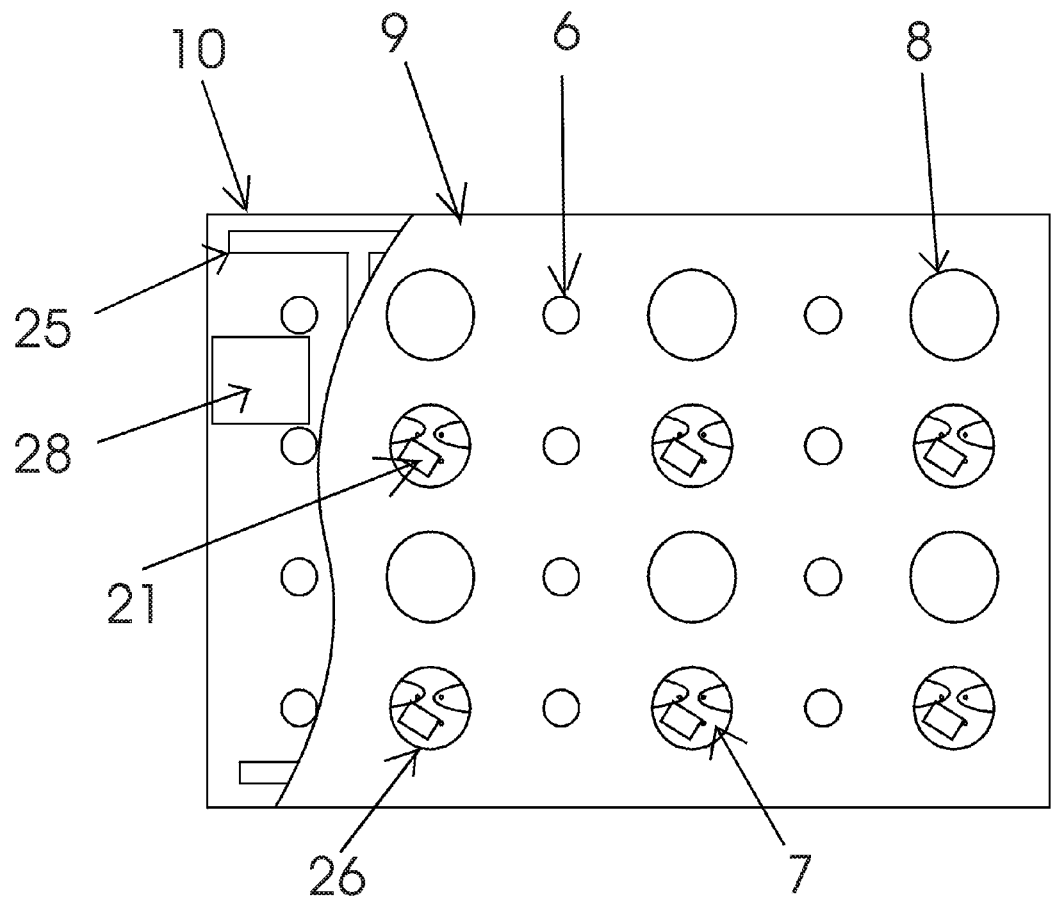
FIG. 7 is a view of the present invention looking at the electrical connection side of the semiconductor laser diode and lens sets from inside the high pressure air cavity. This view shows in detail the arrangement of the tops of the cooling air tubes and spacers, the tops of the standoff posts, the connection terminals of the semiconductor laser diode and lens sets, the automatic power control circuit electronic modules, the sensor and voltage data computer processor and the flexible, non-stretchable membrane (9) with holes cut directly adjacent to the semiconductor laser diode and lens sets to facilitate cooling from above.
Figure 8:
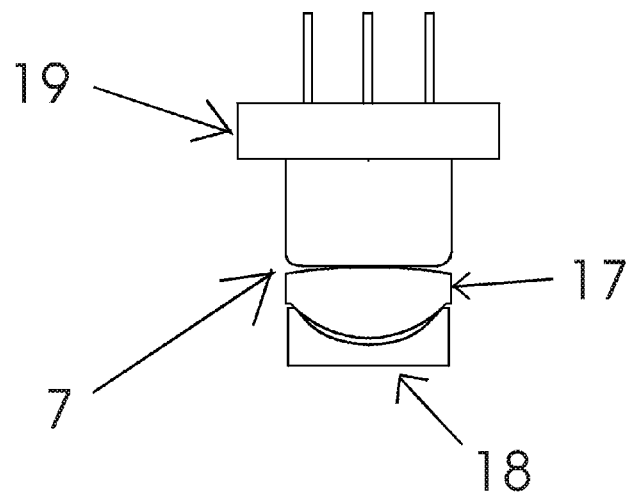
FIG. 8 is a side view of the present invention showing in detail the arrangement of the semiconductor laser diodes, the collimating lens and the plano-concave lens.
Figure 19:
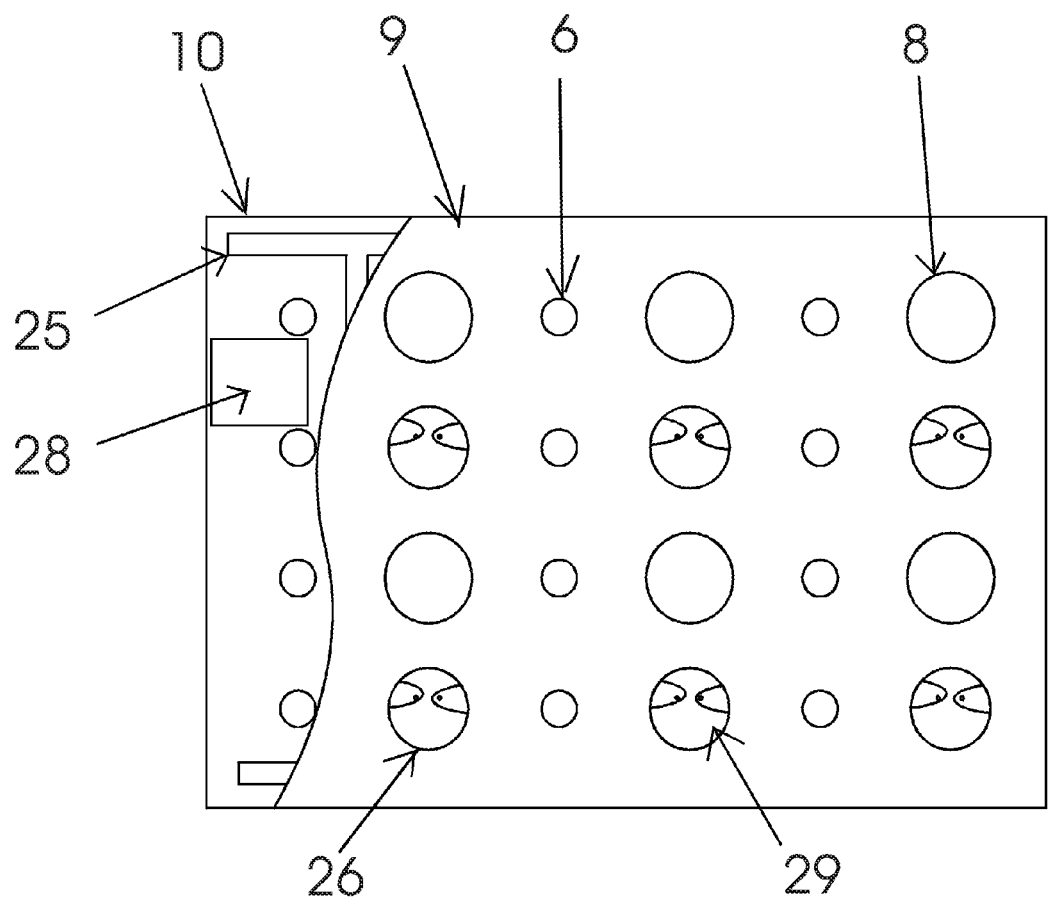
FIG. 19 is a view of the present invention looking at the electrical connection side of the light emitting diode and lens sets from inside the high pressure air cavity. This view shows in detail the arrangement of the tops of the cooling air tubes and spacers, the tops of the standoff posts, the connection terminals of the light emitting diode and lens sets, the sensor and voltage data computer processor and the flexible, non-stretchable membrane (9) with holes cut directly adjacent to the light emitting diode and lens sets to facilitate cooling from above.
Figure 20:
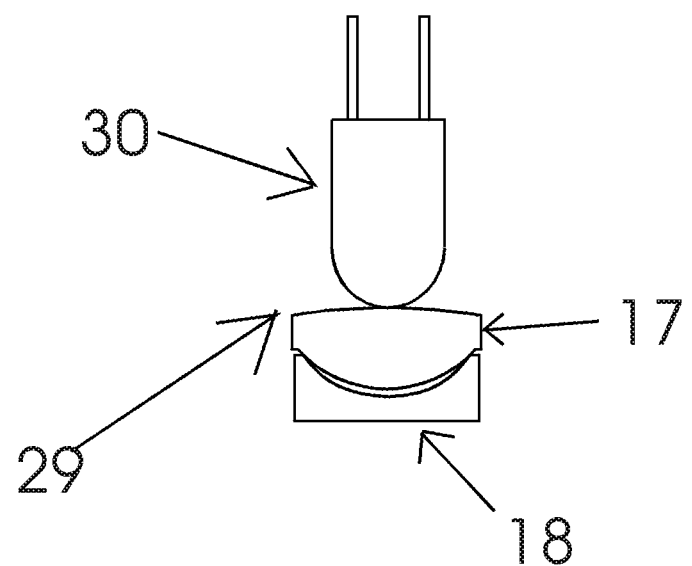
FIG. 20 is a side view of the present invention showing in detail the arrangement of the light emitting diodes, the collimating lens and the plano-concave lens.
Figure 21:
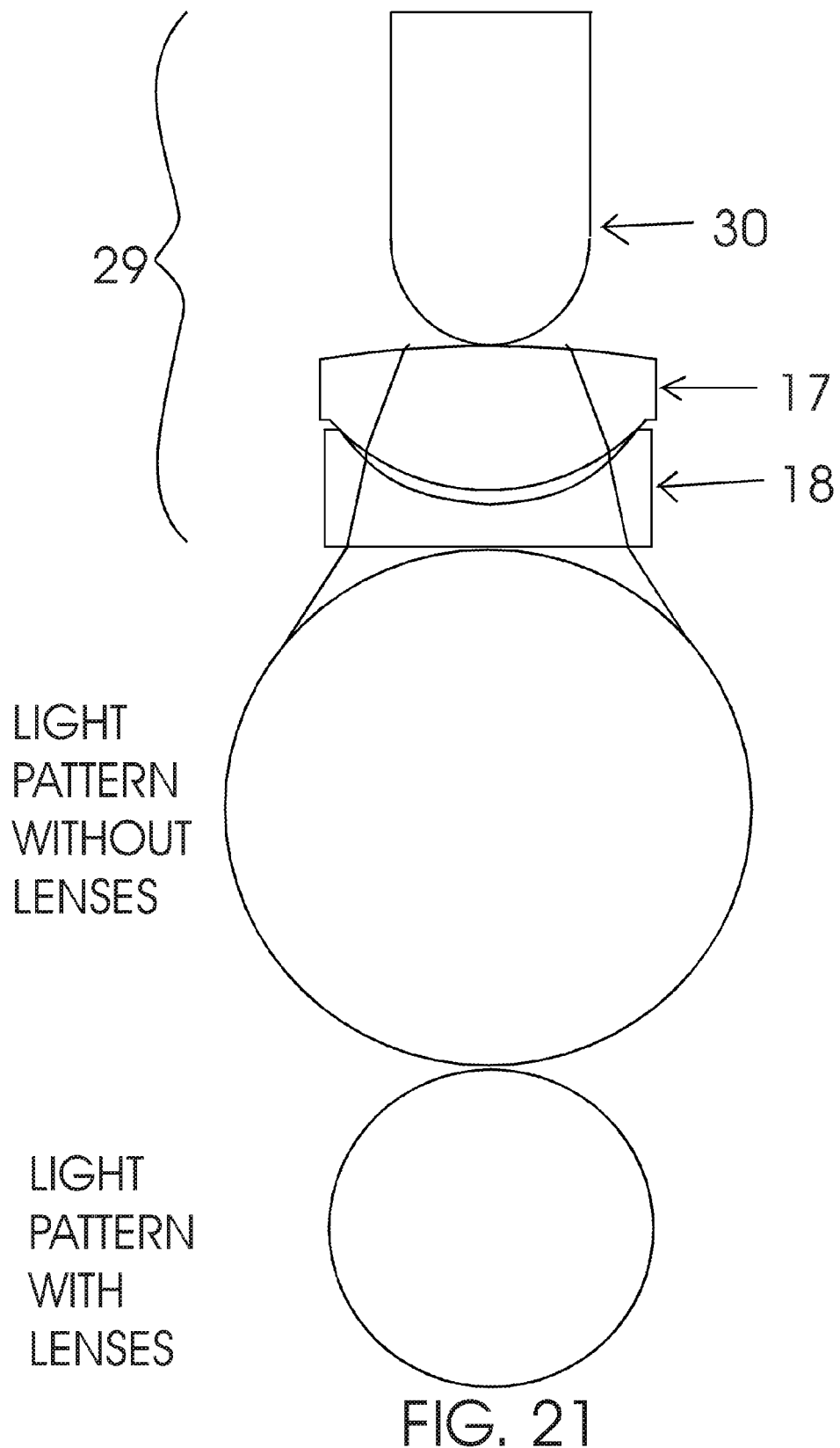
FIG. 21 is a view of the present invention showing in detail the light emitting diode and lens sets collimating and then spreading the light of the diode. This view shows the light pattern from a LED with no lenses and light through both lenses.

Referring now to FIG. 7 and FIG. 19 of the drawings, reference numeral (26) refers to the one or more holes in membrane (9) directly adjacent to the non-emission side of the one or more lasers (7) or the LEDs (29). Reference numeral (21) refers to the one or more automatic power control circuit electronic modules and reference numeral (25) refers to the flat braided and/or non-braided electrical conductors. The one or more holes (26) allow high pressure air to cool the one or more power control (21) and the electrical connection pins of the one or more lasers (7) or the one or more LEDs (29) and conductors (25). This cooling effect in conjunction with the cooling effect on the front side of the one or more lasers (7) or LEDs (29) discussed above maintains the one or more lasers (7) or LEDs (29) at the optimal temperature for light propagation.

Figure 6:
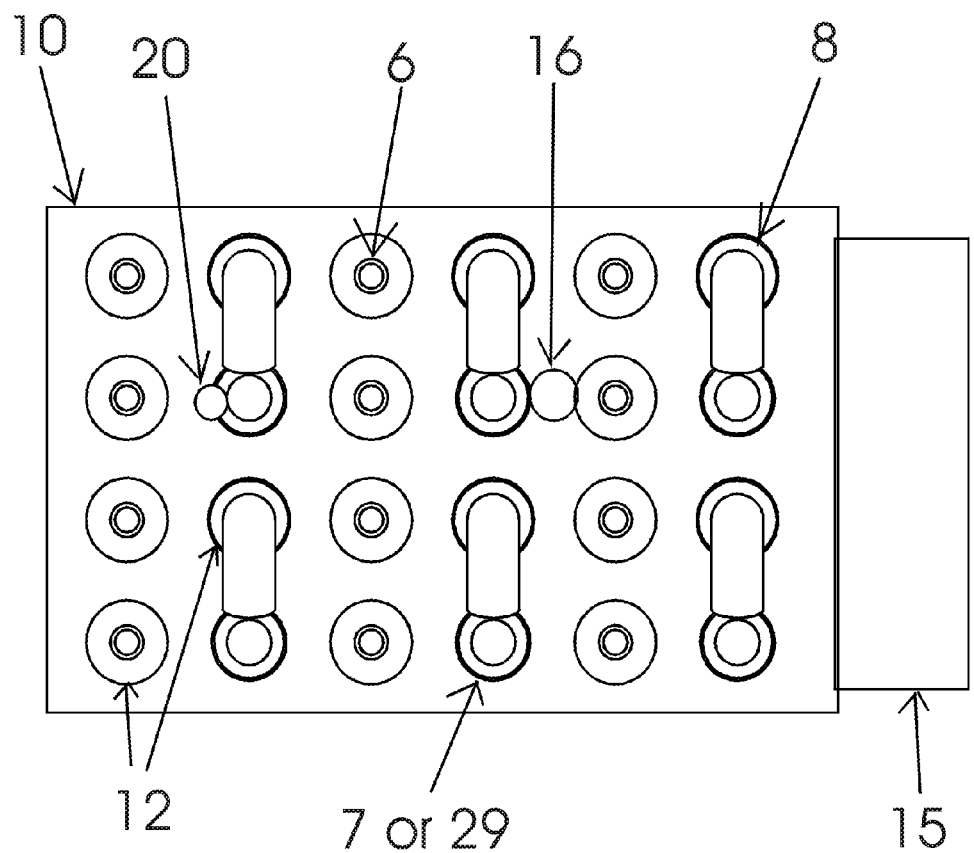
FIG. 6 is a view looking at the light emission side of the present invention showing in detail the arrangement of the semiconductor laser diode and lens sets or the LED and lens sets, the cooling air tubes and spacers, the infrared radiation sensors, the temperature sensors, the standoff posts, the flexible membrane with bonded flat braided and/or non-braided electrical conductors and the capacitive proximity sensors.

Referring now to FIG. 6 of the drawings, reference numeral (20) refers to one or more temperature sensors bonded to the radiation emitting side of the one or more lasers (7) or LEDs (29).

Referring now to FIG. 1 of the drawings, reference numeral (14) refers to an electrical cable for power and data communication and reference numeral (4) refers to power supply and computer control with wireless communication.

Referring now to FIG. 1 and FIG. 5 and FIG. 6 and FIG. 7 of the drawings, the output of the one or more temperature sensors (20) is transmitted to the sensor and voltage data computer processor (28) where the temperature of the one or more lasers (7) or LEDs (29) is analyzed. The sensor and voltage data computer processor (28) then sends timing information to regulate the speed of the one or more fans (3) thereby maintaining a constant temperature of the one or more lasers (7) or LEDs (29). The one or more lasers (7) or LEDs (29) receive power from the conductors (25) which in turn receive power from power cable (14) which in turn receives power from computer control (4).

Referring now to FIG. 1 and FIG. 6 of the drawings, reference numeral (16) refers to one or more infrared radiation sensors and reference numeral (15) refers to one or more capacitive proximity sensors. The one or more sensors (16) sense ambient light infrared radiation and infrared radiation from the patient's treatment area. The one or more sensors (15) sense a capacitive increase from the patient's treatment area when in close contact with the patient's treatment area. The one or more sensors (16) and the one or more sensors (15) send data to the sensor and voltage data computer processor (28) where analysis of infrared radiation and the capacitance information determines if the TLD is in close contact with the patient's treatment area. The infrared radiation must be below what is received from ambient light (high threshold) and must be equal to or greater than what is expected from the treatment area of a patient (low threshold). If the infrared radiation is equal to or greater than the low threshold and below the high threshold the computer (28) then checks the capacitance value. If both the infrared radiation levels and the capacitance levels are within range the computer sends a signal to the touch screen computerized device with wireless communication reference numeral (5) and will allow a therapy session to begin when initiated by computerized device (5). If during the therapy session either the one or more sensors (15) or the one or more sensors (16) present data to computer processor (28)

which is out of range computer processor (28) will send a signal by way of power supply and computer control (4) to computerized device (5) and computerized device (5) will terminate the therapy session. This function ensures that light radiation is directed onto the patient's treatment area and not in a direction that would potentially cause harm. It also protects against malicious use of the TLD. In addition to the functions described above computerized device (5) displays information to the user, communicates with the computer control (4) via wireless communication, initiates a therapy session, terminates a therapy session, maintains therapy duration timing, lets a user set therapy duration, displays to the user the elapsed time and the time left in the therapy session, displays to the user battery charge level and prohibits the initiation of a therapy session if battery charge is below a prescribed level, lets a user set light power level, lets the user set the total therapy dosage, calculates the light power level and therapy duration based on total therapy dosage, lets the user choose between continuous or pulsed light operation, stores previous therapy session data and lets the user select a previously stored therapy regimen, lets a medical professional transmit a therapy regimen to the touch screen computerized device with wireless communication via the internet or cellular telephone and monitor the status of the TLD and the number of therapy sessions completed, sounds an audible signal when a therapy session is initiated, sounds an audible signal when a therapy session is terminated, waits a standard length of time after the audible signal before initiating laser or LED power, sounds an audible alarm in the case the TLD becomes separated from the patient's treatment area, warns the user of problems encountered by the TLD, shuts the TLD down in the event of malfunction, lets the user pause the therapy session and restart the therapy session, displays a standard laser warning message about laser safety, maintains a constant wireless communication dialog with computer control (4) and in the event the communication dialog is broken computer control (4) terminates the therapy session. The communication transmission between the computerized device with wireless communication and the power supply and computer control is encrypted for security as is the transmission over the internet or cellular phone. The touch screen computerized device with wireless communication is either a made for purpose device programmed to perform the functions described above and provided with the TLD or it is an application program (computer code) loadable to a cellphone, touch screen tablet, lap top computer or a desk top computer which has been approved and certified as being capable of performing the stated functions.

Figure 4:
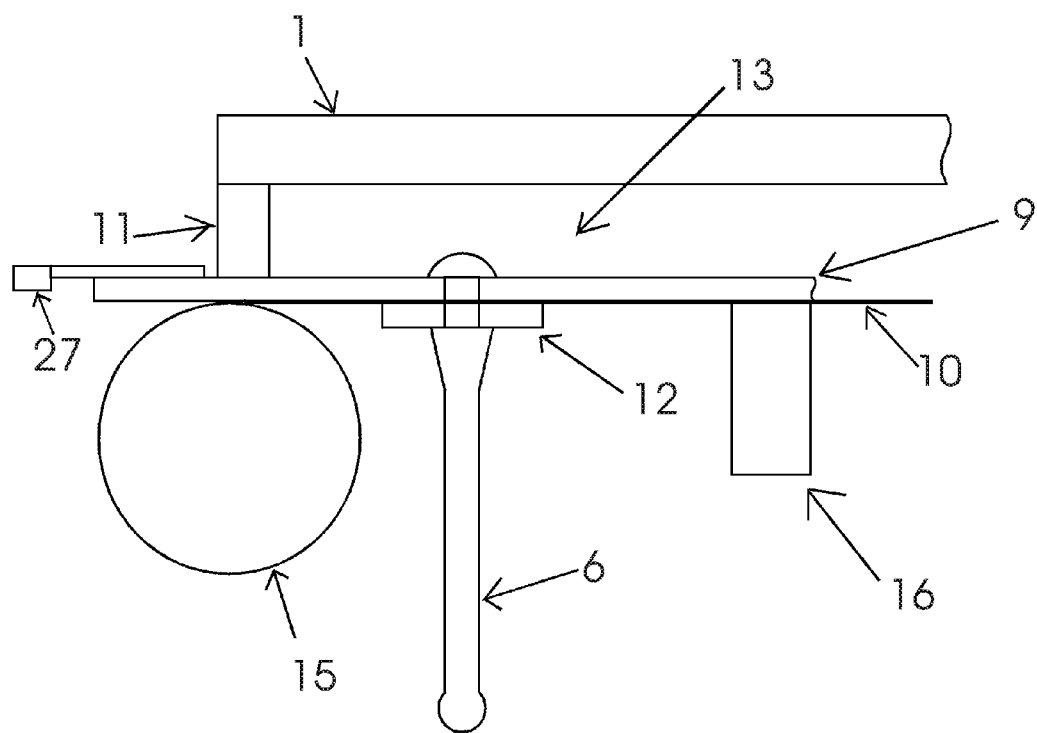
FIG. 4 is a side view of the present invention showing in detail the arrangement of the standoff posts in relation to the capacitive proximity sensors, the infrared radiation sensors and the high pressure air cavity.
Figure 10:
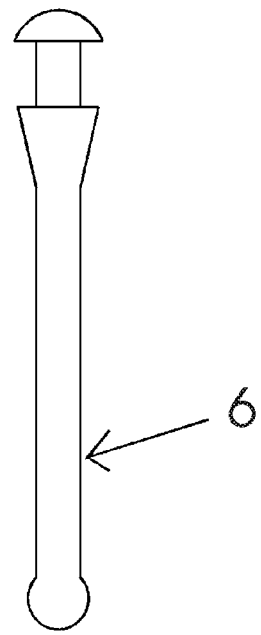
FIG. 10 is a side view of the present invention showing in detail the standoff posts.
Figure 11:
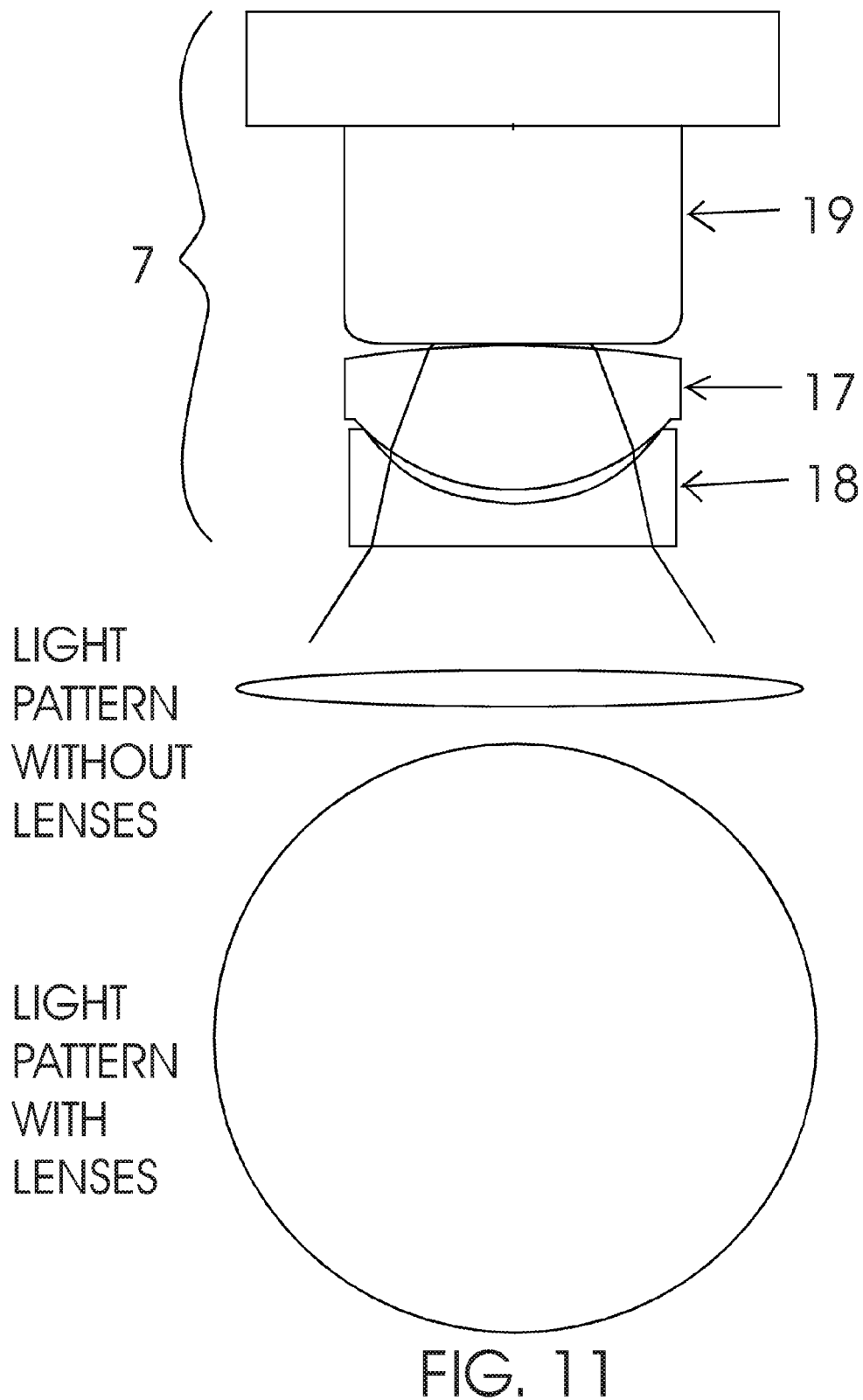
FIG. 11 is a view of the present invention showing in detail the semiconductor laser diode and lens sets collimating and then spreading the laser light of the diode. This view shows the light pattern from a laser with no lenses and laser light through both lenses.

Referring now to FIG. 4 and FIG. 5 and FIG. 10 of the drawings, reference numeral (6) refers to the one or more standoff posts. Membrane (9) is attached to flexible membrane with bonded flat braided and/or non-braided electrical conductors, reference numeral (10) by means of the one or more standoff posts which penetrate and hold together membrane (9) and membrane (10). Membrane (10) can be made of polyimide, polyester, polyethylene napthalate, or polyetherimide among others. The one or more standoff posts provide, in addition to their attachment function, a separation function between the lasers (7) or LEDs (29) and the surface area to be treated on a patient. Reference numeral (12) refers to one or more flexible membrane washers which add rigidity to the standoff posts (6). The standoff posts are formed to present a small cross sectional area to the laser or LED light so as to not block a large degree of the laser or LED light from reaching the treatment area.

Figure 9:
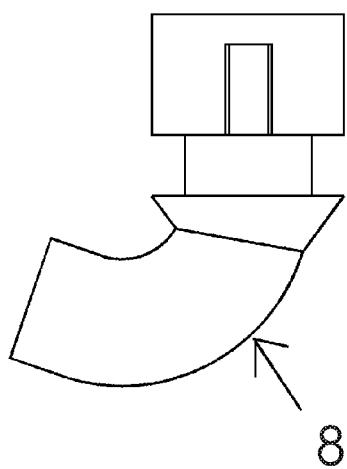
FIG. 9 is a side view of the present invention showing in detail the cooling air tubes and spacers.

Referring now to FIG. 3 and FIG. 9 of the drawings, reference numeral (12) refers to one or more flexible membrane washers which add rigidity to the one or more air tubes (8).

Referring now to FIG. 8, FIG. 11, FIG. 20 and FIG. 21 of the drawings, reference numeral (19) refers to the one or more semiconductor laser diodes, reference numeral (30) refers to the one or more light emitting diodes, reference numeral (17) refers to the one or more collimating lenses and reference numeral (18) refers to one or more plano-concave lenses which in combination comprise the one or more lasers (7) or LEDS (29). The light emitted by the one or more diodes (19) is in the form of an ellipse as indicated by 'LIGHT PATTERN WITHOUT LENSES' on FIG. 11. The light emitted by lasers (7) after passing through the one or more lenses (17) and (18) is in the form of a circle as indicated by 'LIGHT PATTERN WITH LENSES' on FIG. 11. This light pattern transformation is necessary to produce and even distribution of laser light radiation under each of the one or more lasers (7) to affect a uniform dosage. The light emitted by the one or more diodes (30) is in the form of a large circle as indicated by 'LIGHT PATTERN WITHOUT LENSES' on FIG. 21. The light emitted by LEDs (29) after passing through the one or more lenses (17) and (18) is in the form of a small circle as indicated by 'LIGHT PATTERN WITH LENSES' on FIG. 21. This light pattern transformation is necessary to produce and even distribution of LED light radiation under each of the one or more LEDs (29) to affect a uniform dosage. The standoff posts (6) are formed in such a way that the distance between the lasers (7) or LEDs (29) and the patient's treatment area is optimized such that the entire treatment area is uniformly radiated with the prescribed dosage.

Figure 12:
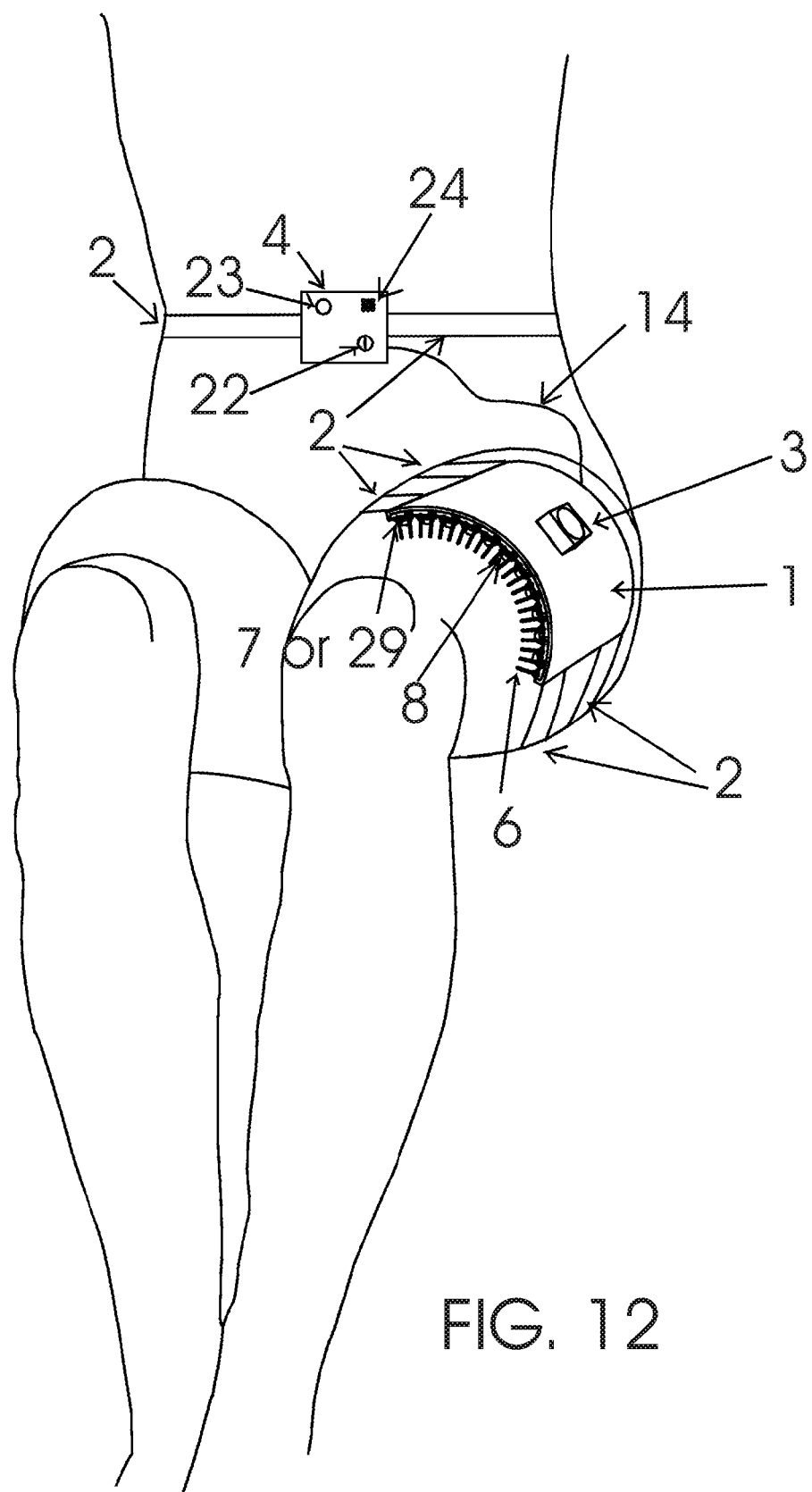
FIG. 12 is a view showing one possible embodiment of the present invention with all the major assemblies depicted in a usable arrangement on the leg of a patient.

Referring now to FIG. 1 and FIG. 3 and FIG. 12 of the drawings, reference numeral (2) refers to stretchable straps with hook and loop fasteners. The stretchable straps with hook and loop fasteners (2) enable the TLD to be fixed to a patient in a manner that allows movement of the area to be treated and movement of the patient within and without the treatment premises. The stretchable straps with hook and loop fasteners (2) are connected to the TLD with zippers, reference numeral (27), to enable quick removal for cleaning and replacement. The movement of the patient must not exceed the maximum range of the communication capability between computer control (4) and computerized device (5) or the therapy session will be terminated by computer control (4). Computer control (4) also has stretchable straps with hook and loop fasteners (2). Computer control (4) can provide power either by battery or by connection to mains power at the wall. Computer control (4) maintains the voltage and current to the semiconductor lasers or LEDs within close tolerances to ensure the correct laser or LED power and dosage levels. Computer control (4) contains a key lock reference numeral (22) which provides security against unauthorized use, a laser radiation full duration indicator light reference numeral (23) which provides laser-on or LED-on indication and a laser radiation momentary at start audible signal device reference numeral (24) which provides an indication of the beginning of a therapy session.

Figure 13:
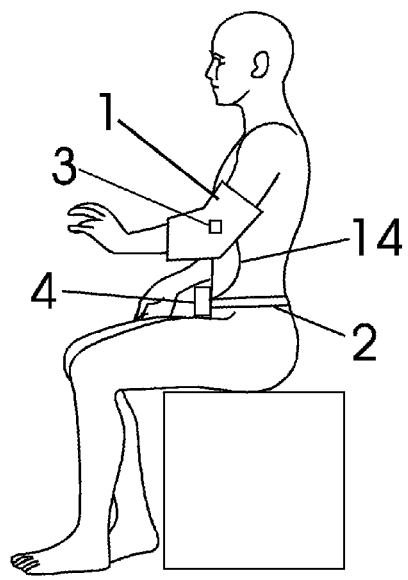
FIG. 13 is a view showing a second possible embodiment of the present invention depicted in a usable arrangement on the elbow of a patient.
Figure 14:
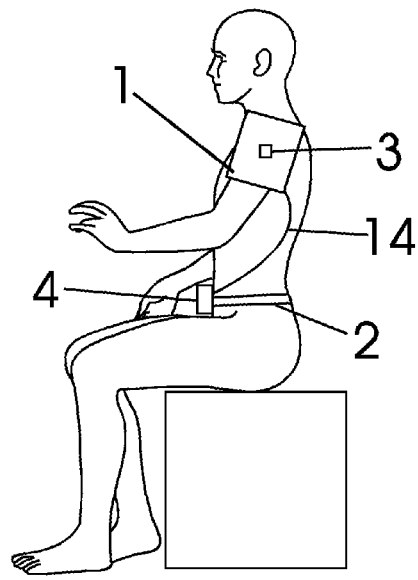
FIG. 14 is a view showing a third possible embodiment of the present invention depicted in a usable arrangement on the shoulder of a patient.
Figure 15:
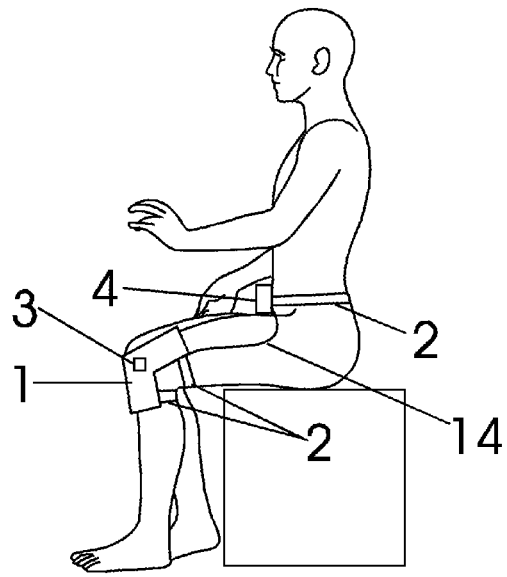
FIG. 15 is a view showing a fourth possible embodiment of the present invention depicted in a usable arrangement on the knee of a patient.
Figure 16:
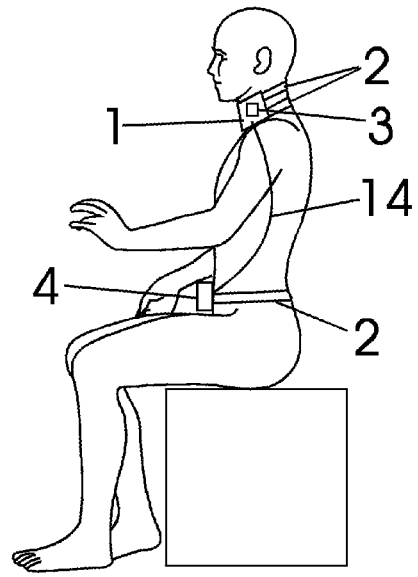
FIG. 16 is a view showing a fifth possible embodiment of the present invention depicted in a usable arrangement on the neck of a patient.

Referring now to FIG. 13, FIG. 14, FIG. 15 and FIG. 16 of the drawings show additional possible embodiments of the present invention but do not limit the potential embodiments that could be created using the same technology. FIG. 13 shows an embodiment designed for the elbow. FIG. 14 shows an embodiment designed for the shoulder. FIG. 15 shows an embodiment designed for the knee. FIG. 16 shows an embodiment designed for the neck. Additional embodiments could include but are not limited to the lower back, the ankle, the top of the foot, the bottom of the foot, the head, the hand, the buttocks, the lower leg, the face, etc.

Figure 17:
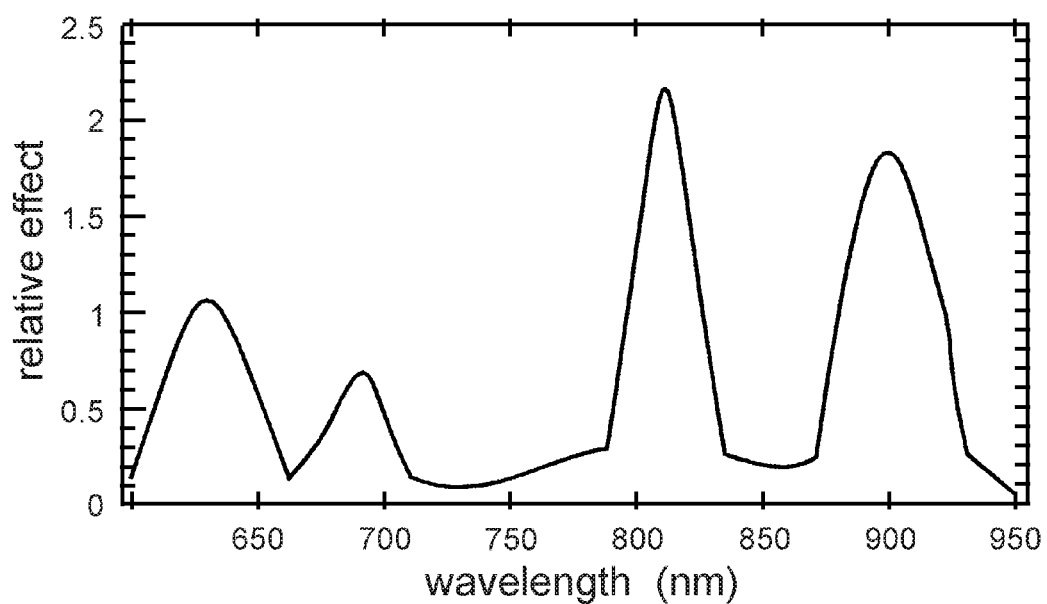
FIG. 17 is a graph of Generalized Action Spectrum for LLLT effects in cells, animals and patients.
Figure 18:
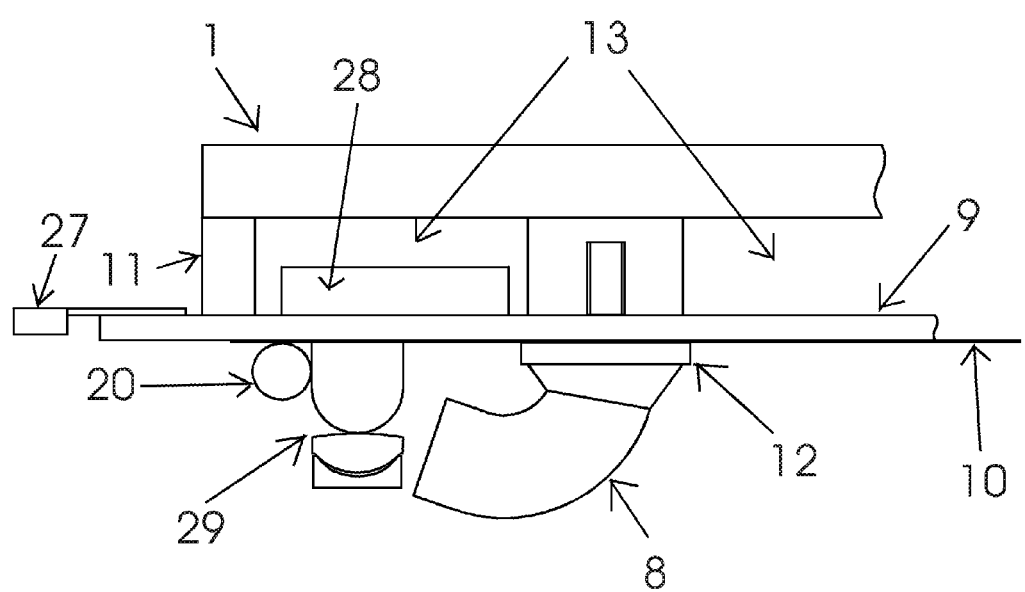
FIG. 18 is a side view of the present invention showing in detail the arrangement of the cooling air tube and spacer in relation to the light emitting diode and lens sets, the high pressure air cavity, the temperature sensors and the sensor and voltage data computer processor.

Referring to FIG. 17 of the drawings it is shown that physiological activity affected by laser or LED light energy is not uniform but is greater in certain wavelengths than others.

What is claimed is:

1. A therapeutic laser or light emitting diode device (laser device) comprising:
    a plurality of semiconductor laser diodes or light emitting diodes (LEDs) arranged in a two dimensional array bonded to a first flexible membrane with bonded flat braided and non-braided electrical conductors (10), each semiconductor laser diode or light emitting diode positioned for emitting coherent or non-coherent electromagnetic radiation in the range 380 nm to 1,400 nm in a direction perpendicular to the first flexible membrane (10);
    a second flexible, non-stretchable membrane (9) attached to the first flexible membrane (10), on the side opposite to that of the plurality of semiconductor laser diodes or light emitting diodes, by a plurality of standoff posts penetrating both membranes and affecting a union between the first flexible membrane (10) and the second flexible, non-stretchable membrane (9), wherein the plurality of standoff posts are configured to contact a treatment area and thereby provide a predetermined distance between the treatment area and the plurality of semiconductor laser diodes or light emitting diodes;
    a narrow, stretchable, flexible closed cell membrane (11);
    one or more high pressure fans with speed control and air filters;
    a stretchable, flexible closed cell membrane (1);
    one or more capacitive proximity sensors which detect an increase of capacitance when in close contact with a patient's treatment area;
    one or more infrared radiation sensors which detect infrared radiation from ambient light and infrared radiation from the patient's treatment area;
    one or more temperature sensors which detect the temperature of the plurality of semiconductor laser diodes or light emitting diodes;
    a plurality of cooling air tubes and spacers each associated with one of the plurality of semiconductor laser diodes or light emitting diodes which channel and direct cooling air from the high pressure air cavity in a curved path onto the light emitting side of the semiconductor laser diodes or light emitting diodes;
    a plurality of automatic power control circuit electronic modules each associated with one of the plurality of semiconductor laser diodes:
    a sensor and voltage data computer processor.

2. The laser device of claim 1 wherein the one or more capacitive proximity sensors, the one or more infrared radiation sensors and the one or more temperature sensors send their data to the sensor and voltage data computer processor which after analysis sends commands through the electrical cable for power and data communication to the power supply and computer control with wireless communication which in turn transmits sensor data to the touch screen computerized device with wireless communication for user notification and display and laser device control.

3. The laser device of claim 2 wherein the sensor and voltage data computer processor analyzes the output of the one or more temperature sensors and sends timing information to regulate the speed of the one or more high pressure fans with speed control and air filters thereby maintaining a constant temperature of the plurality of lasers or light emitting diodes.

4. The laser device of claim 2 wherein the sensor and voltage data computer processor analyzes:
    the output of the one or more infrared radiation sensors to determine if the infrared radiation level is below what is expected from ambient light (high threshold) and equal to or greater than what is expected from the treatment area of a patient (low threshold);
    the output of the one or more capacitive proximity sensors to determine if the capacitive value is that which is expected when in close contact with a patient's treatment area;
    and prevents laser or light emitting diode radiation from being energized if either the infrared radiation sensor data or the capacitive sensor data is out of range thereby ensuring that laser or light emitting diode radiation is directed onto the patient's treatment area and not in a direction that would potentially cause harm.

5. The laser device of claim 2 wherein the sensor and voltage data computer processor analyzes all voltage levels using reference voltage technology and transmits instructions to the power supply and computer control with wireless communication through the electrical cable for power and data communication to adjust the voltages within specified ranges or sends a voltage-out-of-range signal to the power supply and computer control with wireless communication which then terminates the therapy session and initiates warning messages.

* * * * *